US006384288B1

(12) United States Patent
Kühling et al.

(10) Patent No.: US 6,384,288 B1
(45) Date of Patent: May 7, 2002

(54) METHOD FOR THE PRODUCTION OF BIS (4-HYDROXYARYL)ALKANES

(75) Inventors: Steffen Kühling, Niklaas (BE); Rolf Lanze; Rainer Neumann, both of Krefeld (DE); Frieder Heydenreich, Düsseldorf (DE); Tony van Osselaer, Krefeld (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/807,645

(22) PCT Filed: Oct. 5, 1999

(86) PCT No.: PCT/EP99/07358

§ 371 Date: Apr. 16, 2001

§ 102(e) Date: Apr. 16, 2001

(87) PCT Pub. No.: WO00/23410

PCT Pub. Date: Apr. 27, 2000

(30) Foreign Application Priority Data

Oct. 17, 1998 (DE) .......................... 198 48 026

(51) Int. Cl.⁷ .................. C07C 37/68; C07C 39/00; C07C 39/12; C07C 39/16
(52) U.S. Cl. .................. 568/724; 568/716; 568/717; 568/722; 568/723
(58) Field of Search ................. 568/724, 723, 568/722, 717, 716

(56) References Cited

U.S. PATENT DOCUMENTS

| | | | | |
|---|---|---|---|---|
| 2,775,620 A | | 12/1956 | Williamson | 260/619 |
| 4,859,803 A | | 8/1989 | Shaw | 568/727 |
| 4,931,146 A | | 6/1990 | Iimuro et al. | 203/92 |
| 5,091,159 A | | 2/1992 | Connelly et al. | 423/122 |
| 5,629,457 A | * | 5/1997 | Zhang et al. | 568/724 |
| 5,648,561 A | * | 7/1997 | Tan et al. | 568/727 |

* cited by examiner

Primary Examiner—Samuel Barts
Assistant Examiner—Elvis O. Price
(74) Attorney, Agent, or Firm—Joseph C. Gil; Aron Preis

(57) ABSTRACT

A process for producing bis(4-hydroxyaryl)alkane is disclosed. The process comprise in sequence the steps of (a) passing inert gas through a melt at 150 to 230° C. that contains bis(4-hydroxyaryl)alkane and other aromatic hydroxy compounds, under conditions designed to remove said other aromatic hydroxy compounds from said melt and to obtain a stream of inert gas that contains said other aromatic hydroxy compounds (b) condensing the stream obtained in (a) to remove said other aromatic hydroxy compound, and to obtain a stream of inert gas, and (c) purifying and compressing the stream of inert gas obtained in (b), and recycling to step (a).

10 Claims, No Drawings

METHOD FOR THE PRODUCTION OF BIS (4-HYDROXYARYL)ALKANES

The present invention relates to a process for producing bis(4-hydroxy-aryl)alkanes from addition products of bis(4-hydroxy-aryl)alkanes and aromatic hydroxy compounds which are obtained by the acid-catalysed reaction of aromatic hydroxy compounds with ketones.

The synthesis of bis(4-hydroxyaryl)alkanes by the acid-catalysed reaction of aromatic hydroxy compounds with ketones is known from U.S. Pat. No. 2,775,620 or EP-A 342 758 for example. As a rule, an addition product of the bis(4-hydroxyaryl)alkane and of the aromatic hydroxy compound which is used as a starting material is obtained as an intermediate, and is subsequently freed from the aromatic hydroxy compound by distillation. The most important example of large-scale industrial production is the production of bisphenol A, during which an addition product of bisphenol A (BPA) and phenol is obtained as an intermediate. Even after purification, by recrystallisation for example, this addition product still contains traces of acid (about 5 to $10.10^{-6}$ mol acid/mol BPA) due to the acid-catalysed production route employed. On the separation of the phenol from bisphenol A, which is associated with an increase in temperature, these traces of acid result in the partial decomposition of the bisphenol and in the formation of by-products. The consequence of these decomposition reactions is an impairment of the purity and quality of colour of the bisphenol. This also has a negative effect on the quality of products produced from the bisphenols, such as epoxy resins, polyesters, polyester carbonates and polycarbonates, the consequences of which are problems of colour, poor transmission of light through transparent products, or pinholes in the surfaces of mouldings produced from these end products. Similar phenomena also occur during the production of other bis(4-hydroxyaryl)alkanes.

The separation of the aromatic hydroxy compound, which is also termed "stripping", from the bis(4-hydroxyaryl)alkane, is known from the literature and is described in EP-A 343 349 for example. The aromatic hydroxy compound is separated from the bis(4-hydroxyaryl) alkane here by employing steam in a packed column at 160 to 200° C. under a slightly reduced pressure. It is also known, e.g. from U.S. Pat. No. 5,091,159, that thermal decomposition reactions occur during the separation of the aromatic hydroxy compound from the bis(4-hydroxyaryl) alkane.

A process has now been found which strongly suppresses decomposition reactions during the stripping of the aromatic hydroxy compound ("monophenol") from the bis(4-hydroxyaryl)-alkane. On the separation of the monophenol from the bis(4-hydroxyaryl)alkane with inert gas in the course of this process, the recycled inert gas is purified after the condensation of the monophenol, so that degradation of the bis(4-hydroxyaryl)alkane can be avoided.

The addition products of bis(4-hydroxy-aryl)alkanes and aromatic hydroxy compounds which can be used in the process according to the invention can be obtained by the reaction of aromatic hydroxy compounds which are not substituted in the p-position and which contain no second order substituents such as cyano, carboxy or nitro groups, for example phenol, o- and m-cresol, 2,6-dimethylphenol, o-tert.-butyl phenol, 2-methyl-6-tert.-butylphenol, o-cyclohexylphenol, o-phenylphenol, o-isopropylphenol, 2-methyl-6-cyclopentyl-phenol, o- and m-chlorophenol, 2,3,6-trimethylphenol, preferably phenol, o- and m-cresol, 2,6-dimethylphenol, o-tert.-butylphenol and o-phenyl-phenol, most preferably phenol, with ketones which comprise at least one aliphatic group on their carbonyl function, for example acetone, methyl ethyl ketone, methyl propyl ketone, methyl isopropyl ketone, diethyl ketone, acetophenone, cyclohexanone, cyclopentanone, and methyl-, dimethyl- and trimethylcyclohexanones which may also contain geminal methyl groups e.g. 3,3-di-methyl-5-methylcyclohexanone (hydroisophorone), preferably acetone, acetophenone, cyclohexanone and homologues thereof which contain methyl groups, most preferably acetone. The addition product of bisphenol A and phenol is preferably used as a starting material.

The present invention thus relates to a process for producing bis(4-hydroxyaryl)alkanes from addition products of bis(4-hydroxyaryl)alkanes and aromatic hydroxy compounds, wherein a) an inert gas is passed through a melt of an addition product of a bis(4-hydroxyaryl)alkane and an aromatic hydroxy compound at 150° C. to 230° C., wherein the inert gas stream removes the aromatic hydroxy compound from the melt, b) the aromatic hydroxy compound is removed from the inert gas stream by condensation, c) the inert gas stream is purified, compressed and recycled to step a).

Separation of the monophenol from the bis(4-hydroxyaryl)alkane from the melt of the addition product of bis(4-hydroxyaryl)alkane and aromatic hydroxy compound is effected at temperatures between 150° C. and 230° C., preferably from 170° C. to 210° C., by expelling the monophenol by the introduction of an inert gas (e.g. nitrogen). The ratio of gas to the amount of addition product is preferably about 10 $m^3$ to 1000 $m^3$ per tonne of addition product. Stripping can optionally be facilitated by reducing the pressure in the processing unit which is used for the separation of the monophenol, but is preferably effected under normal pressure. Stripping of the monophenol by the inert gas is conducted in known apparatuses, for example in a packed, flooded column. The monophenol can be removed from the inert gas circulation system, for example, by condensation on a heat exchanger.

Purification of the recirculated inert gas can be effected by passing it over a fixed bed adsorbent (activated carbon, zeolite etc.), or in one preferred embodiment can be effected by intensively scrubbing the inert gas. This scrubbing step can be effected in a gas scrubber for example. In one preferred embodiment, during the compression of the inert gas of the circulating flow in a compressor the sealing liquid which is employed there is used as the scrubbing medium.

A slightly alkaline aqueous solution is used as the scrubbing medium. The pH of the aqueous solution which is used should fall within the range from 7 to 12, preferably from 7.5 to 11, most preferably from 8 to 10. All substances which exhibit a basic effect can be used for the production of an aqueous solution such as this. Alkali and alkaline earth hydroxides are preferred. In one preferred embodiment, the pH is monitored before and after scrubbing, so that excessive and insufficient additions are prevented during the purification of the circulating gas circuit. Moreover, the inert gas stream can subsequently be fed to a second scrubbing step. The second scrubbing medium preferably has a neutral pH.

The bis(4-hydroxyaryl)alkanes which are produced by the process according to the invention are distinguished by their very good inherent colour and by their high purity. In particular, they comprise low contents of aromatic hydroxy compounds (<100 ppm, preferably <50 ppm) and of decomposition products (e.g. isopropenylphenol, dimeric isopropenylphenol).

Polymers such as polycarbonates or epoxides which exhibit a low degree of inherent colour can be manufactured from bis(4-hydroxyaryl)-alkanes which are produced by the process according to the invention.

EXAMPLES

Example 1

A molten mixture of BPA and phenol (60/40% by weight) was fed into a desorber at a rate of 1 tonne/hour. 225 m$^3$/hour of nitrogen (as a circulating flow) were passed continuously into the desorber. The phenol was taken up by the nitrogen and was subsequently condensed by means of a heat exchanger. The nitrogen was subsequently fed to a compressor, the sealing liquid of which was acted upon by very dilute NaOH solution (pH 10), where the nitrogen was compressed. The nitrogen was then introduced into a gas scrubber which was operated using deionised water. The nitrogen which was treated in this manner was then reused in the desorber for the stripping of phenol. A low-phenol (phenol content 40 ppm), light-coloured BPA melt was then obtained, which had a melt Hazen colour of 8.

Comparative example 1

The procedure was as in Example 1, except that scrubbing of the nitrogen was completely omitted. A BPA was then obtained which had a Hazen colour of 17. The phenol content of the BPA was 90 ppm, which indicated decomposition.

Comparative example 2

The procedure was as in Example 1, except that neutral deionised water (pH 6.9) was used for scrubbing the nitrogen. A BPA was then obtained which had a Hazen colour of 14. The phenol content of the BPA was 75 ppm, which again indicated decomposition.

Comparative example 3

The procedure was as in Example 1, except that a dilute NaOH solution (pH 13) was used for scrubbing the nitrogen. A BPA was then obtained which had a Hazen colour of 12. The phenol content of the BPA was 60 ppm, which still indicated decomposition.

We claim:
1. A process for producing bis(4-hydroxyaryl)alkanes from addition products of bis(4-hydroxyaryl)alkanes and aromatic hydroxy compounds, wherein
   a) an inert gas is passed through a melt of an addition product of a bis(4-hydroxy-aryl)alkane and an aromatic hydroxy compound at 150° C. to 230° C., wherein the inert gas stream removes the aromatic hydroxy compound from the melt,
   b) the aromatic hydroxy compound is removed from the inert gas stream by condensation,
   c) the inert gas stream is purified, compressed and recycled to step a).
2. A process according to claim 1, wherein purification of the inert gas stream is effected by scrubbing with an aqueous medium with a pH within the range from 7 to 12.
3. A process according to claim 2, wherein the sealing liquid of the compressor used for the compression of the inert gas is employed as the scrubbing medium.
4. A process according to claim 2, wherein after alkaline scrubbing and before it is recycled to step a) the inert gas stream is subjected to a second scrubbing step in an aqueous medium of neutral pH.
5. A process according to claim 1, wherein purification of the inert gas stream is effected by passing it over a fixed bed adsorbent.
6. A process according to claim 5, wherein activated carbon or zeolite is used as the fixed bed adsorbent.
7. A process for producing bis(4-hydroxyaryl)alkane comprising in sequence the steps of
   (a) passing inert gas through a melt at 150 to 230° C. that contains bis(4-hydroxyaryl)alkane and other aromatic hydroxy compounds, under conditions designed to remove said other aromatic hydroxy compounds from said melt and to obtain a stream of inert gas that contains said other aromatic hydroxy compounds,
   (b) condensing the stream obtained in (a) to remove said other aromatic hydroxy compound, and to obtain a stream of inert gas, and
   (c) purifying and compressing the stream of inert gas obtained in (b), and recycling to step (a).
8. The process of claim 7 wherein purifying is effected by scrubbing with an aqueous medium having a pH of 7 to 12.
9. The process of claim 7 wherein purifying is effected by passing the stream of inert gas over a fixed bed absorbent.
10. The process of claim 9 where the absorbent is a member selected from the group consisting of activated carbon and zeolite.

* * * * *